(12) United States Patent
Yan et al.

(10) Patent No.: US 10,746,652 B1
(45) Date of Patent: Aug. 18, 2020

(54) HEMOGLOBIN SENSOR AND DETECTING METHOD THEREOF

(71) Applicant: REDEYE INC., Hsinchu (TW)

(72) Inventors: Shuo-Ting Yan, Hsinchu (TW); Kuan-Wei Su, Hsinchu (TW); I-Hua Wang, Hsinchu (TW); Chen-Chung Chang, Hsinchu (TW)

(73) Assignee: REDEYE INC., Hsinchu (TW)

( * ) Notice: Subject to any disclaimer, the term of this patent is extended or adjusted under 35 U.S.C. 154(b) by 0 days.

(21) Appl. No.: 16/374,218

(22) Filed: Apr. 3, 2019

(51) Int. Cl.
| | |
|---|---|
| *G01N 21/31* | (2006.01) |
| *G01N 33/49* | (2006.01) |
| *G01N 33/483* | (2006.01) |
| *A61B 10/00* | (2006.01) |
| *G01N 33/493* | (2006.01) |

(Continued)

(52) U.S. Cl.
CPC ......... *G01N 21/31* (2013.01); *A61B 10/0038* (2013.01); *G01N 21/27* (2013.01); *G01N 33/487* (2013.01); *G01N 33/4833* (2013.01); *G01N 33/49* (2013.01); *G01N 33/493* (2013.01); *G01N 33/721* (2013.01); *G01N 2201/0221* (2013.01)

(58) Field of Classification Search
CPC .. A61B 10/0038; G01N 33/48; G01N 33/483; G01N 33/4833; G01N 33/487; G01N 33/48707; G01N 33/48785; G01N 33/49; G01N 33/493; G01N 21/3103; G01N 2021/3125; G01N 2021/3129; G01N 2021/3133; G01N 21/314; G01N 21/3151; G01N 21/59; G01N 21/62; G01N 21/63; G01N 21/64; G01N 21/65; G01N 33/721; G01N 21/27; G01N 21/255; G01N 21/31; G01N 2021/0385; G01N 2201/022; G01N 2201/0221; G01N 2201/0222
USPC .......................................................... 356/39
See application file for complete search history.

(56) References Cited

U.S. PATENT DOCUMENTS

| | | | |
|---|---|---|---|
| 2008/0198360 A1* | 8/2008 | Dosmann | G01N 21/255 356/39 |
| 2012/0149126 A1* | 6/2012 | Wilson | B01F 11/0266 436/175 |

(Continued)

FOREIGN PATENT DOCUMENTS

CN         109297946 A   *   2/2019

*Primary Examiner* — Gordon J Stock, Jr.
(74) *Attorney, Agent, or Firm* — Chun-Ming Shih

(57) ABSTRACT

A hemoglobin sensor capable of quickly detecting occult blood of excreta in a toilet and a detecting method thereof are disclosed. The hemoglobin sensor includes a handheld housing and a result presentation unit. The housing includes a light emitting unit, an operating interface, a light sensing unit, and a data processor disposed therein. The operating interface is connected to the light emitting unit for activating the light emitting unit to emit a plurality of incident light beams having wavelengths in a range between 350 nm and 800 nm. The incident light beams penetrate a solution in a container having excreta and hit a light reflector of the container to produce at least one detection light beam. The light sensing unit receives the detection light beam and output a detection signal, and the data processor generates a detection result data after receiving the detection signal and analyzing it. The result presentation unit receives the detection result data and shows whether occult blood is present in the excreta.

12 Claims, 11 Drawing Sheets

(51) Int. Cl.
*G01N 33/72* (2006.01)
*G01N 21/27* (2006.01)
*G01N 33/487* (2006.01)

(56) References Cited

U.S. PATENT DOCUMENTS

| | | | | |
|---|---|---|---|---|
| 2012/0262703 | A1* | 10/2012 | Zahniser | G01N 15/1475 |
| | | | | 356/39 |
| 2013/0336567 | A1* | 12/2013 | Chan | G01N 21/6456 |
| | | | | 382/133 |
| 2017/0082602 | A1* | 3/2017 | Pyayt | A61B 5/14552 |
| 2017/0212039 | A1* | 7/2017 | Yan | G01J 3/0264 |
| 2018/0085098 | A1* | 3/2018 | Attar | A61B 10/0038 |
| 2019/0323949 | A1* | 10/2019 | Carvalho Sousa | ............... |
| | | | | G01N 33/4833 |
| 2020/0150030 | A1* | 5/2020 | Yan | G01N 33/4833 |

* cited by examiner

HEMOGLOBIN SENSOR AND DETECTING METHOD THEREOF

FIELD OF THE INVENTION

The invention relates to a hemoglobin sensor and a detecting method thereof, more particularly, to a hemoglobin sensor capable of detecting occult blood inside the excreta in the toilet, which can effectively enhance the accuracy and convenience of occult blood inspection in excreta.

BACKGROUND

Hemoglobin is a substance normally found in blood, and therefore detection of hemoglobin is one of the major methods for preventing and treating most illness at early stage, for example, stool occult blood testing for colorectal cancer, urine occult blood testing for bladder cancer or kidney cancer, sputum occult blood testing for bronchitis or lung tumor, etc.

In Taiwan, colon cancer rate has topped the cancer ranking for eleven consecutive years and is also the highest in the world. The incidence rate and death rate of colon cancer patients are respectively 18.6% and 20.1% in China, which both topped the rankings in the world. The incidence rate for colon cancer is 8% out of all cancer patients, which ranks fourth and the death rate ranks second in USA. Hence, improving the accuracy and convenience of stool occult blood test is an important factor for early treatment of colon cancer to lower the death rate.

However, conventional stool occult blood test requires collecting fecal specimen, sending it to the hospital for testing and waiting for the test result, which not only is inconvenient for the patient, the inability of testing-at-anytime also prohibits self-management of the patient for long-term health monitoring.

Moreover, the specimen collected for conventional testing is about 1 gram, but only 6 milligrams is used by the medical unit for testing. However, occult blood in the stool is not distributed evenly and so false negative result is easily concluded from the testing when the occult blood was not collected in the specimen. In addition, the bleeding of tumor or polyp is periodic, not continuous, and so it is possible that the tumor or the polyp did not bleed on the day of or the day before the collection of stool specimen, causing the test result to be false negative. Hence, the presence of occult blood in excreta cannot be accurately known and in turn the patient cannot be treated in time.

SUMMARY

An objective of the invention is to provide a hemoglobin sensor that can detect the presence of occult blood in human excreta or pet excreta at any time, and not only the convenience, accuracy and speediness of the occult blood test can be enhanced, the effect of long-term tracking, portability, early-finding and early treatment of illness can be achieved.

Another objective of the invention is to provide a method of detecting hemoglobin with simple and easy steps to test for occult blood in the excreta, and thereby realizing effective health monitoring at home.

To achieve the objectives mentioned above, the present invention provides a hemoglobin sensor, which includes a handheld housing and a result presentation unit. The handheld housing includes and has disposed therein: a light emitting unit disposed in the housing for generating a plurality of incident light beams with wavelengths in a range between 350 nm to 800 nm; an operating interface connected to the light emitting unit for activating the light emitting unit to emit the incident light beams toward a front end of the housing; a light sensing unit disposed in the housing for receiving at least one detection light beam and generating a detection signal; and a data processor connected to the light sensing unit for receiving the detection signal and generating a detection result data. The result presentation unit receives the detection result data and shows a detection result. The incident light beams are aimed at a solution that is in a container having an excreta and external of the housing, and the incident light beams penetrate the solution and produce the detection light beam.

The present invention provides a method for detecting hemoglobin, which includes: providing a handheld hemoglobin sensor with a light emitting unit and operating the light emitting unit to emit a plurality of incident light beams that penetrate a solution in a container having an excreta and produce a plurality of detection light beams, wherein the container is a toilet, a bedpan, a urinal, a portable urinal, or a spittoon; providing a light sensing unit to receive the detection light beams and generate a detection signal; providing a data processor to receive the detection signal and generate a detection result data; and providing a result presentation unit to receive the detection result data and present a detection result.

In one embodiment of the invention, the container is a toilet, a bedpan, a urinal, a portable urinal, or a spittoon.

In one embodiment of the invention, the hemoglobin sensor further includes a light guide unit disposed in the housing at a front end of the light sensing unit for collecting and transmitting the detection light beams.

In one embodiment of the invention, the result presentation unit is disposed in a remote electronic device external of the housing or on a surface of the housing.

In one embodiment of the invention, the hemoglobin sensor further includes a probe unit. The probe unit is a hollow tube and is attachable to the front end of the housing. The probe unit includes a light reflector disposed at its front end, wherein the incident light beams hit the light reflector to produce the detection light beams after penetrating the solution. The probe unit has at least one through hole disposed on the hollow tube for the solution to flow into and out of the probe unit.

In one embodiment of the invention, the hemoglobin sensor further includes a filter unit for covering the probe unit and the solution can pass through the filter unit.

In one embodiment of the invention, the light reflector is an inner surface of the probe unit or a reflector sheet.

In one embodiment of the invention, the incident light beams hit a light reflector after penetrating the solution and produce the detection light beams, wherein the light reflector is an inner surface of the container.

In one embodiment of the invention, the detection signal is a spectrum or a light intensity value.

In one embodiment of the invention, the spectrum is an absorption spectrum, a fluorescence spectrum, a scattering spectrum, or a Raman spectrum.

In one embodiment of the invention, the data processor generates the detection result data by analyzing whether the detection signal includes a characteristic wavelength peak values approximate to 415 nm, 541 nm, and 577 nm.

In one embodiment of the invention, the light emitting unit includes at least three light emitting diodes and the wavelength peak values of the incident light beams are respectively 375 nm, 395 nm, and 415 nm.

In one embodiment of the invention, the light emitting unit includes at least four light emitting diodes, one of which is a white light emitting diode.

In one embodiment of the invention, the hemoglobin detection method further includes a step of providing a probe unit attached to a front end of the hemoglobin sensor, and inserting the probe unit into the solution.

In one embodiment of the invention, the hemoglobin detection method further includes providing a filter unit to cover an outer surface of the probe unit and to be inserted into the solution with the probe unit.

BRIEF DESCRIPTION OF THE DRAWINGS

The structure as well as preferred modes of use, further objects, and advantages of this invention will be best understood by referring to the following detailed description of some illustrative embodiments in conjunction with the accompanying drawings, in which.

DETAILED DESCRIPTION OF THE PREFERRED EMBODIMENTS

The term "solution" in the invention refers to solution excreted or produced directly by human or animal, liquid of the solution, or solution of other solvent; for example, solution in the toilet with excreta such as feces, urine, and/or phlegm therein. The term "occult blood" refers to human or animal blood in the excreta, especially blood that is invisible to human eyes.

Figure 1:
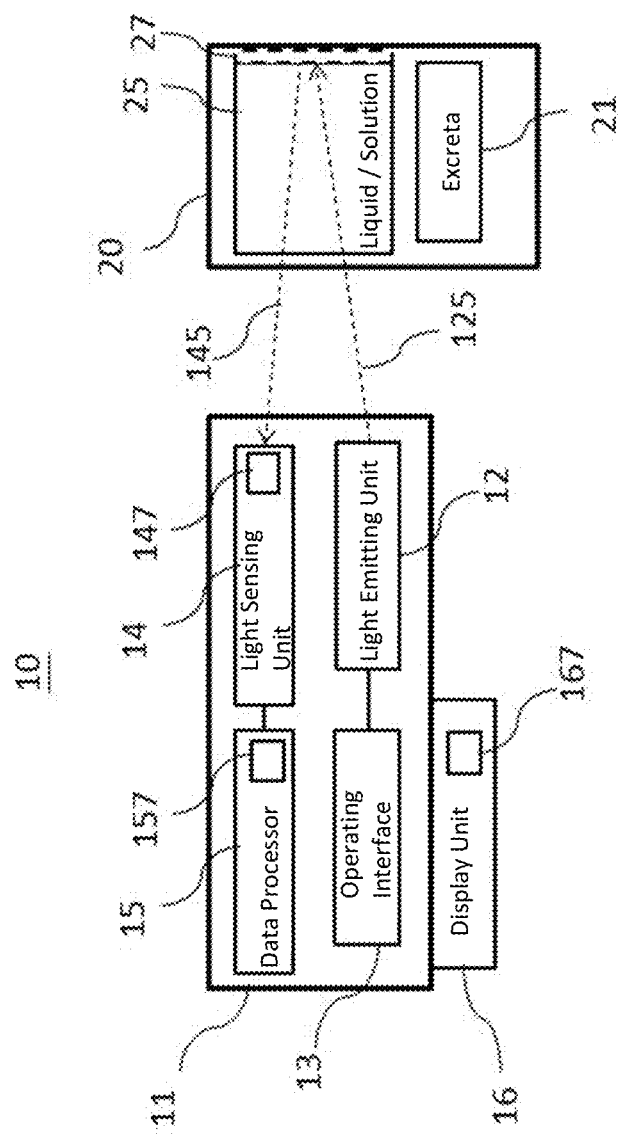
FIG. 1 is a schematic system diagram of a hemoglobin sensor according to an embodiment of the invention.
Figure 2:
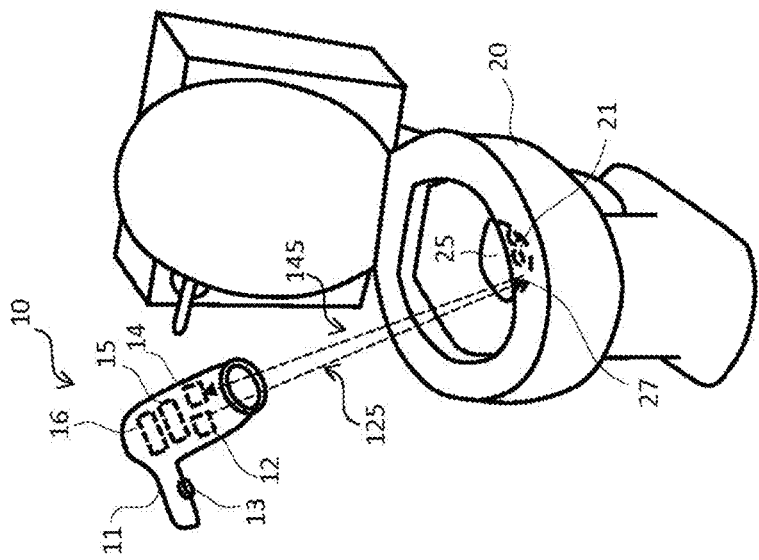
FIG. 2 is a schematic structure diagram of the hemoglobin sensor according to the embodiment shown in FIG. 1

FIGS. 1 and 2 are, respectively, schematic diagrams illustrating a system and a structure of a hemoglobin sensor according to a preferred embodiment of the invention. The hemoglobin sensor 10 of the invention is a handheld sensor and includes a handheld housing 11 and a result presentation unit 16. The handheld housing 11 has, disposed therein, a light emitting unit 12, an operating interface 13, a light sensing unit 14, and a data processor 15. The result presentation unit 16 can be disposed in a remote electronic device that is external of the housing 11, or disposed on a surface of the housing 11 as depicted in this embodiment. The operating interface 13 is connected to the light emitting unit 12 and used to activate the light emitting unit 12 to emit a plurality of incident light beams 125. The incident light beams 125 are projected toward a front end of the housing 11 and aimed at a test solution 25, and in turn produce at least one detection light beam 145. The light sensing unit 14 is securely disposed in the housing 11 to receive the detection light beam 145 and generate a detection signal 147. The data processor 15 is connected to the light sensing unit 14 to receive and analyze the detection signal 147, and then generate a detection result data 157. The result presentation unit 16 is wired or wirelessly connected to the data processor 15 to receive the detection result data 157 and accordingly present a detection result 167 of the occult blood. The results could be presented as, for instance, positive, negative, or occult blood content level (levels 0-5; level 0 means no occult blood, level 5 means serious condition of occult blood presence).

The test solution 25 is stored in a container 20, wherein the container 20 also has an excreta 21 of the person or animal wish to be tested, such as feces, urine, or phlegm. The container 20 is best to be a catching device such as a toilet, a bedpan, a urinal, a portable urinal, or a spittoon, in which the person or animal wish to be tested can directly expel their excreta 21. Since the blood in the excreta 21, if any, would be diluted into the solution 25 and not just be in some parts of the excreta 21, the solution 25 would contain the blood substance. Hence, testing the solution 25 in the container 20 directly is more accurate than testing a section of the excreta 21, and thus the possibility of obtaining a false negative test result is effectively reduced. The incident light beams 125 of the invention are aimed directly at the solution 25 and reflected by a light reflector 27 to form the detection light beam 145, rather than being aimed directly at parts of the excreta 21 itself.

In one embodiment of the invention, the incident light beams 125 can penetrate the test solution 25 and hit the light reflector 27 to produce a detection light beam 145, wherein the light reflector 27 is an inner surface of the container 20, a ceramic reflector, a metal reflector, or a mirror, and so the incident light beams 125 penetrate the solution 25 and hit the light reflector 27, and through the absorption of the solution 25 and the reflection of the light reflector 27, form the detection light beam 145.

Figure 3:
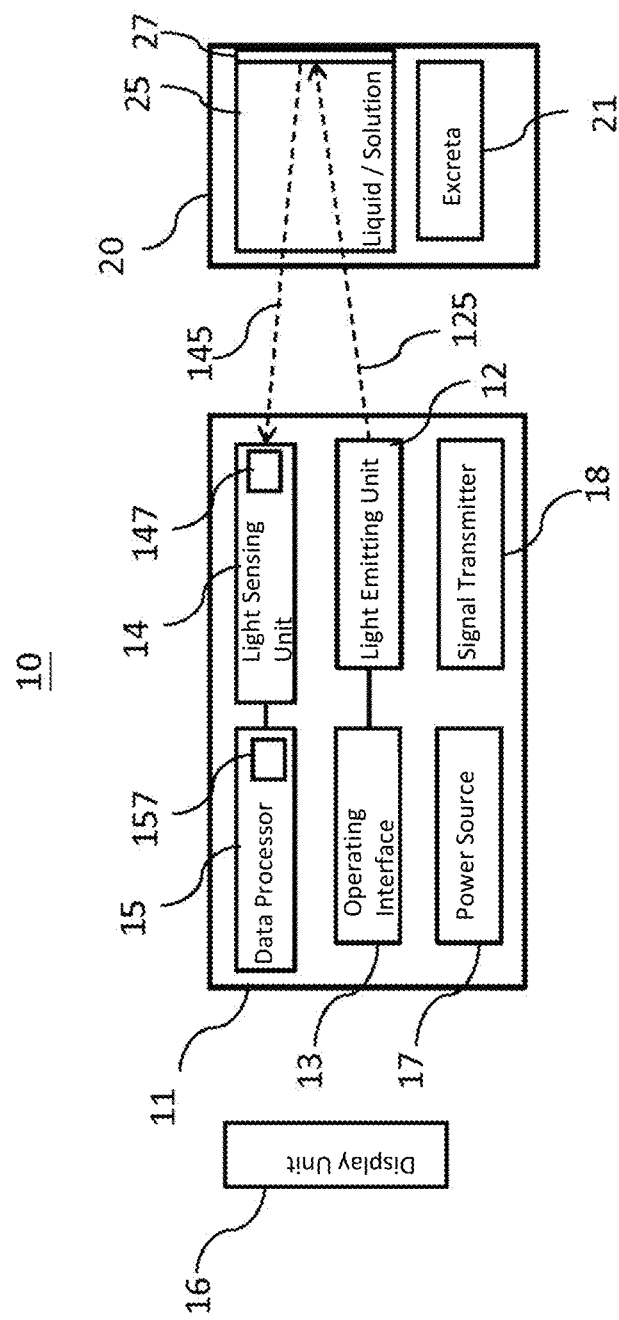
FIG. 3 is a schematic system diagram of a hemoglobin sensor according to another embodiment of the invention.
Figure 4:
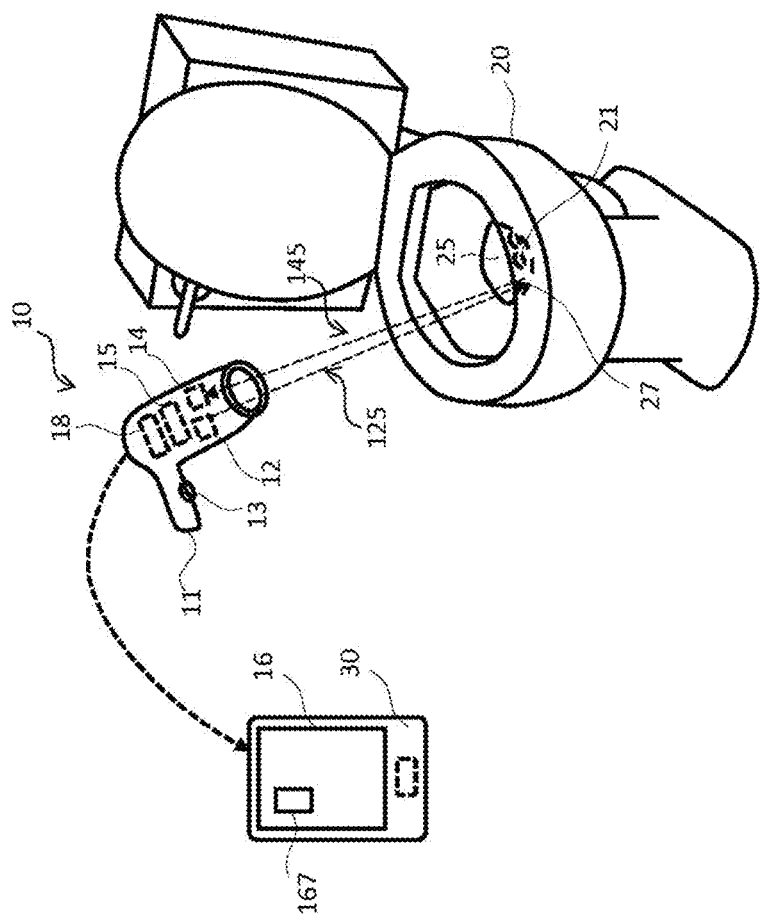
FIG. 4 is a schematic structure diagram of the hemoglobin sensor according to the embodiment shown in FIG. 3.

FIGS. 3 and 4 are respectively schematic diagrams illustrating a system and a structure of the hemoglobin sensor according to another embodiment of the invention. In this embodiment, a power source 17 and a signal transmitter 18 are disposed in the housing 11, and through the signal transmitter 18, the detection result data 157 is transmitted to a remote electronic device 30 external of the housing 11 and the detection result 167 is shown by the result presentation unit 16 disposed in the remote electronic device 30.

Moreover, in one embodiment of the invention, the data processor 15 can also be disposed in the remote electronic device 30 external of the housing 11, wherein the detection signal 147 of the light sensing unit 14 can be transmitted directly to the data processor 15 of the remote electronic device 30 to analyze and generate the detection result data 157 and the detection result 167 by the remote electronic device 30.

In one embodiment of the invention, the power source 17 is lithium battery, mains electricity, or solar power by which power can be transformed and direct current can be output to provide voltage suitable for the light emitting unit 12, the data processor 15, and the light sensing unit 14, like 3V, 3.3V, 5V, etc. The data processor 15 is an ARM Cortex M7 single chip 216 MHz data processor. The operating unit 13 may include power button, start button for testing, and so on. The result presentation unit 16 can have LED lights indicating positive and negative results, battery light indicating remaining capacity, LCD and/or sound units.

Figure 5:
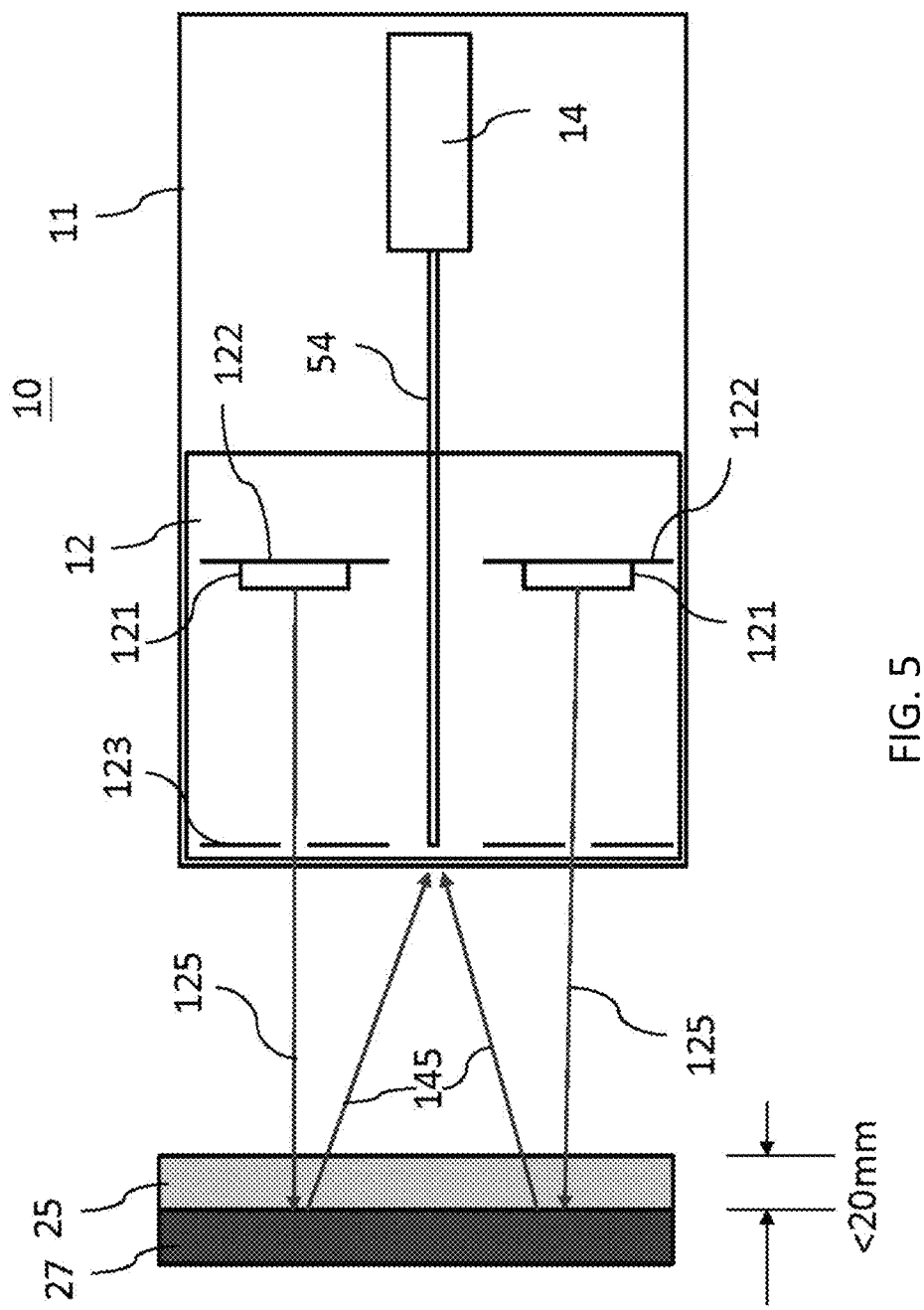
FIG. 5 is a schematic system diagram of a hemoglobin sensor according to yet another embodiment of the invention.

FIG. 5 is a schematic diagram illustrating a system of a hemoglobin sensor according to yet another embodiment of the invention. The hemoglobin sensor 10 further includes a light guide unit 54 disposed in the housing 11 and at a front end of the light sensing unit 14 for collecting and transmitting the detection light beam 145, which in turn enhances the transmission accuracy of the detection light beam 145. In addition, the light emitting unit 12 includes a plurality of light emitting diodes 121, each of which emits an incident light beam 125 with its individual wavelength, and thus together forms the plurality of incident light beams 125 that pass through corresponding slit units 123. The incident light beams 125 penetrate the solution 25 in the container 20 and hit the light reflector 27 to produce the detection light beam 145. The light guide unit 54 collects and transmits the detection light beam 145 to the light sensing unit 14. After the light sensing unit 14 has received the detection light beam 145, a subsequent spectrum characteristic analysis or light intensity value analysis such as absorption spectrum analysis, fluorescence spectrum analysis, scattering spectrum analysis, or Raman spectrum analysis can be conducted to determine the presence of occult blood base on whether hemoglobin exists in the solution 25.

In one embodiment of the invention, the light guide unit 54 is composed of plastic or glass material and is a circular column having a diameter smaller than 3.5 mm. The light emitting diodes 121 of the light emitting unit 12 are secured by a printed circuit board 122 that is made of bonded fiber glass FR4 or aluminum substrate and has a hollow annular shape or a hollow polygonal shape, such that the skinny light guide unit 54 can pass through the center hole of the printed circuit board 122. The light sensing unit 14 is a photo diode array, a CMOS sensor, a CCD sensor, or a photo-spectrometer.

In one embodiment of the invention, the incident light beams 125 penetrate the solution 25 at a relatively shallow region where the depth of the solution 25 is less than 20 mm for obtaining a better collection of the detection light beam 145. The light reflector 27 is an inner surface of the ceramic toilet, and the incident light beams 125 are aimed at a region in the toilet where the water level is lower, and not aimed directly at the excreta itself like the feces.

In one embodiment of the invention, the detection of hemoglobin uses the absorption spectrum analysis, wherein the light emitting unit 12 is a light beam with specific wavelength, like an incident light beam 125 having wavelength within the range of 350 nm-800 nm (nm, nanometer), and the incident light beam 125 passes through the slit unit 123, reaches and penetrates the test solution 25, and hits the light reflector 27 to produce the detection light beam 145. The detection light beam 145 is then directed to the light sensing unit 14 through the light guide unit 54. After the light sensing unit 14 receives the detection light beam 145, the subsequent spectrum analysis is conducted, wherein if the obtained spectrum has a characteristic absorption peak value approximate to 415 nm, 541 nm, or 577 nm, then it is presumed that the hemoglobin in the solution 25 is an indicator for the presence of occult blood and thus the detection result data 157 shows a positive result.

Figure 6:
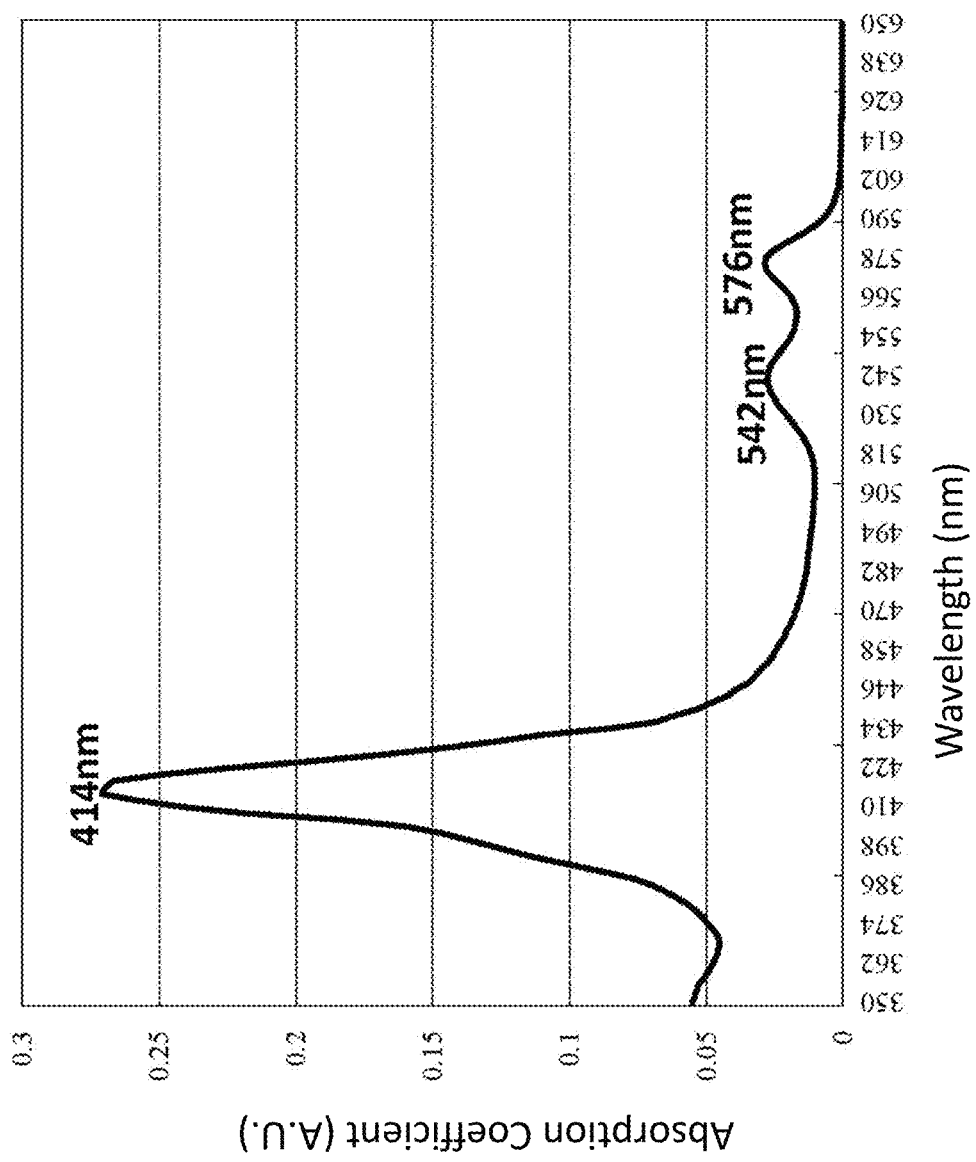
FIG. 6 is a schematic diagram illustrating a wavelength spectrum obtained by the embodied hemoglobin sensor of the invention.

FIG. 6 illustrates the result of hemoglobin signal detected by the embodied hemoglobin sensor of the invention. The actual measurement of absorption spectrum for a solution containing blood with volume concentration of 0.001% is as shown in the figure, which clearly identifies the main characteristic absorption peak values of the blood falls near 414 nm, 542 nm, and 576 nm, matching the characteristic peak values of hemoglobin absorption spectrum.

In yet another embodiment of the invention, the plurality of light emitting diodes 121 is three or four. If the number of light emitting diodes is four, then one of them is a white light emitting diode and the other three are light emitting diodes with wavelength peak values close to 375 nm, 395 nm, and 415 nm. The slit unit 123 can be made of a stainless material, and has a diameter of 0.5 mm-3 mm and a via hole at its center.

When the container 20 has the light reflector 27 that can easily reflect light, the hemoglobin sensor 10 of the invention can be a handheld sensor that can remotely obtain the detection light beam 145, the detection signal 147, the detection result data 157 and the detection result 167 without having to come in contact with the solution 25, and is an easy-to-use, no-chemical-added health monitoring tool in households.

Figure 7:
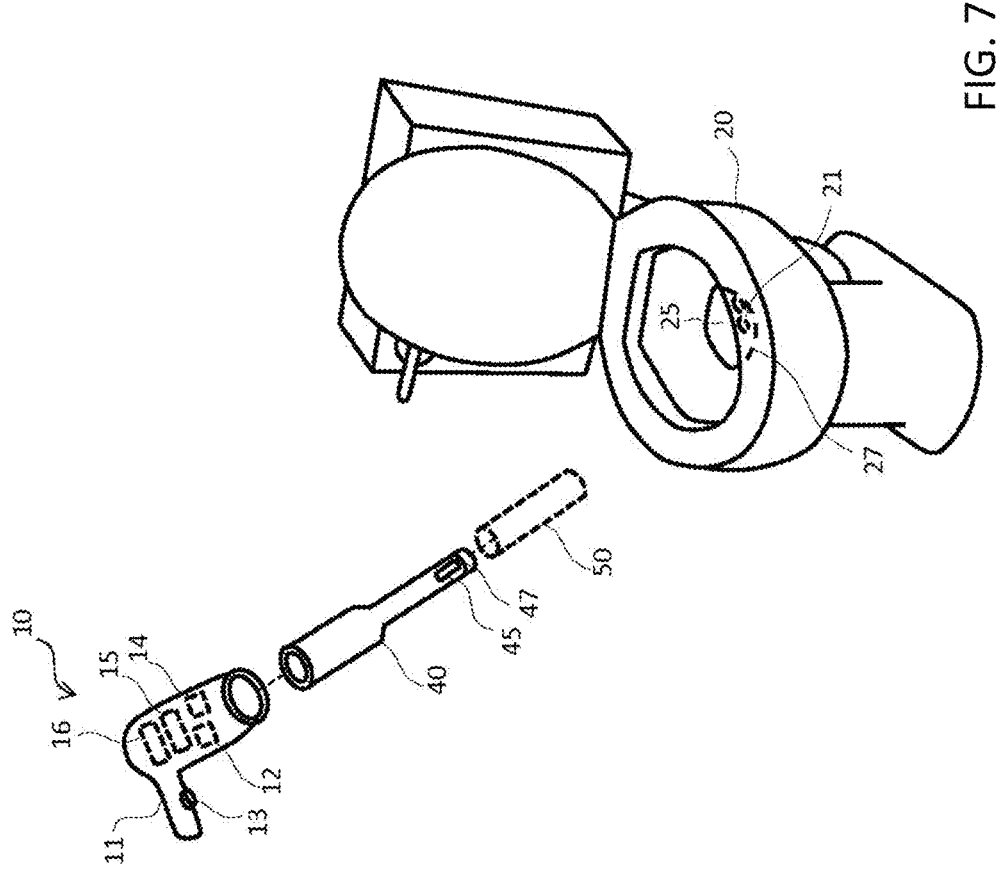
FIG. 7 is a schematic structure diagram of a hemoglobin sensor according to yet another embodiment of the invention.
Figure 8:
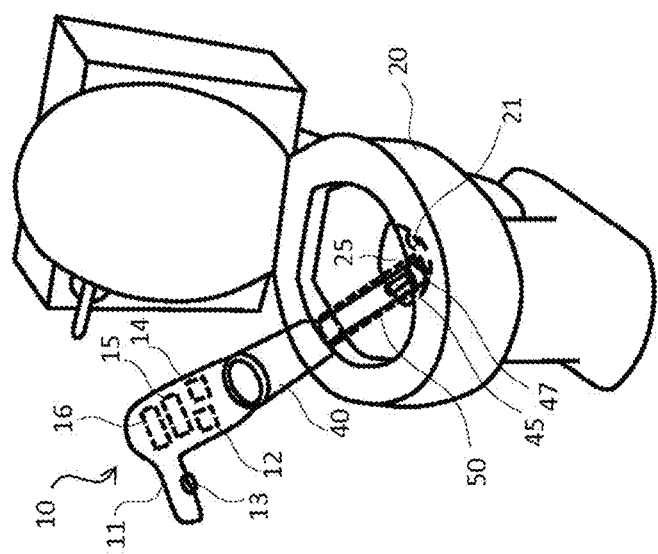
FIG. 8 is a schematic diagram illustrating the hemoglobin sensor according to the embodiment of FIG. 7 in use.

On the other hand, if the container 20 is in a condition where it is difficult to dispose the light reflector 27 therein, the invention further includes a probe unit 40 as shown in FIGS. 7 and 8 for conveniently collecting the detection light beam 145 and thereby achieving the purpose of detecting hemoglobin. The probe unit 40 of the invention is a hollow tube that can be separated, attached and/or fixed to a front end location of the housing 11, and a front end of the probe unit 40 has at least one through hole 45 disposed therein. When the probe unit 40 is inserted into the solution 25 in the container 20, the solution 25 passes through the through hole 45 and flows into the hollow tube of the probe unit 40. The incident light beams 125 penetrate the solution 25 inside the probe unit 40 and hit a light reflector 47 at the front end of the probe unit 40 to produce a detection light beam 145 for subsequent spectrum analysis.

In one embodiment of the invention, the light reflector 47 at the front end of the probe unit 40 is an inner surface of the container 20, an inner surface of the probe unit 40 itself, or a reflector sheet secured on the probe unit 40, wherein the reflector sheet is, but not limited to, a ceramic reflector, a metal reflector, or a mirror.

In one embodiment of the invention, the depth of the solution 25 which the incident light beams 125 are to penetrate needs to be greater than 5 mm (mm, millimeter), for obtaining a better spectrum analysis result; in other words, the probe unit 40 needs to be inserted into the solution for a depth of greater than 5 mm.

In yet another embodiment of the invention, the hemoglobin sensor 10 further includes a filter unit 50. The filter unit 50 can be a circular paper filter cup that jackets and covers the outer surface of the probe unit 40. The filter unit 50 is made of filter material, and when the probe unit 40 is inserted into the solution 25, the filter unit 50 allows the solution 25 to pass through and enter the probe unit 40 via the through hole 45, but blocks large excreta particles or other impurity matter from entering the probe unit 40. Therefore, the reliability of occult blood test result is enhanced.

Figure 9:
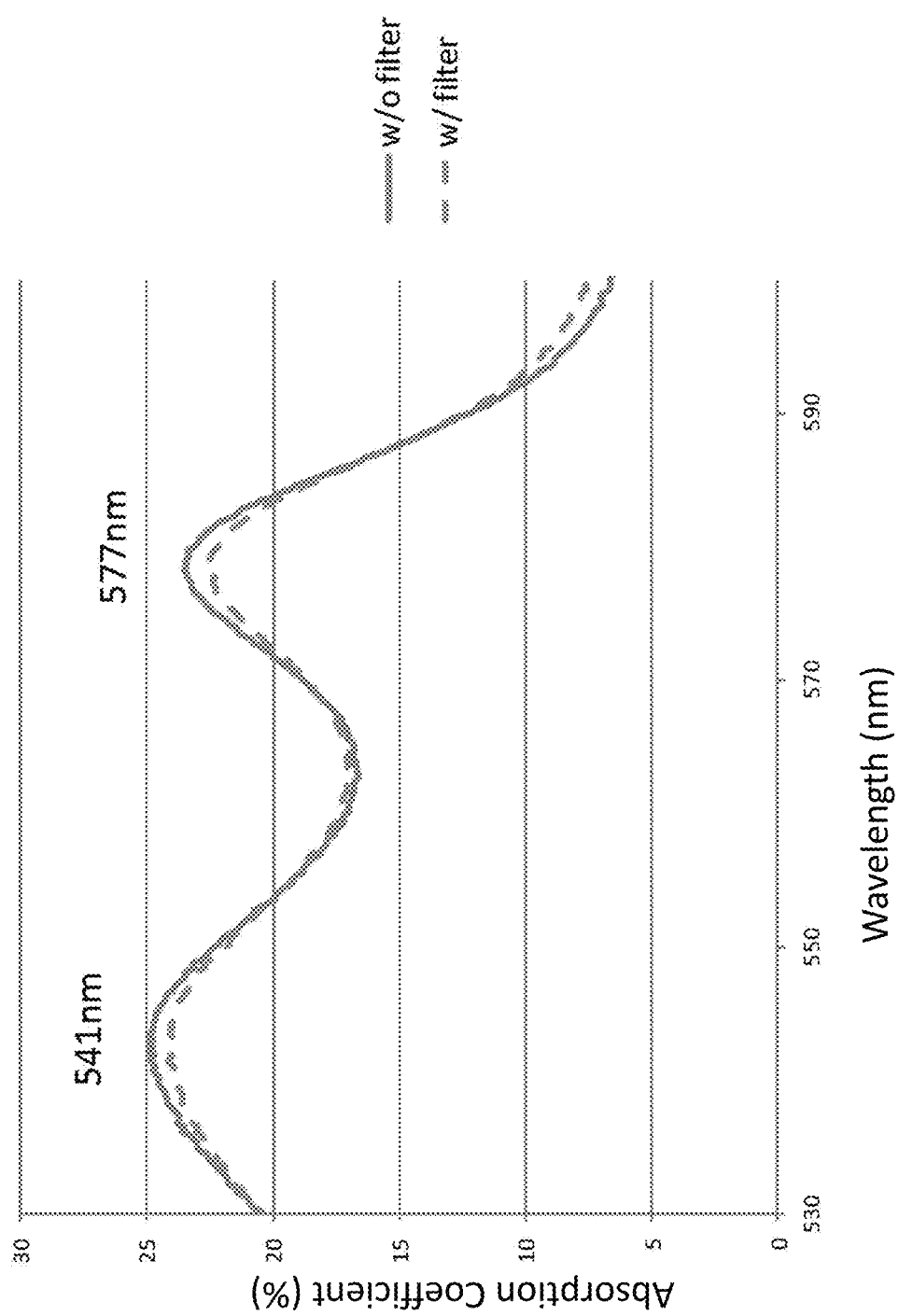
FIG. 9 is a schematic diagram illustrating wavelength spectrums obtained by the hemoglobin sensors of the invention.

As shown in FIG. 9, covering the outer surface of the probe unit 40 with the filter unit 50 does not affect the test result of hemoglobin in the solution 25 performed by the invention. Distinguishable blood absorption peak values close to 541 nm and 577 nm are detected for both testing tools, with and without the filter unit 50.

Figure 10:
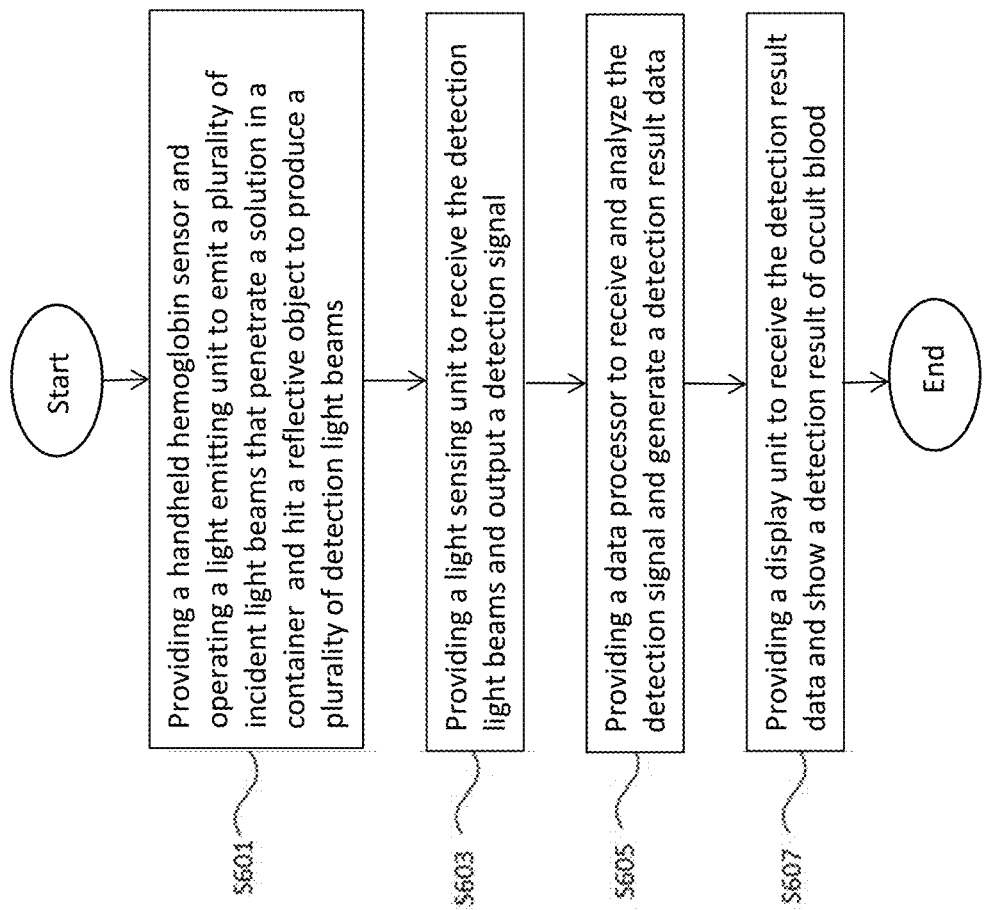
FIG. 10 is a flow chart of a hemoglobin detection method according to an embodiment of the invention.

FIG. 10 is a flow chart illustrating a method of detecting hemoglobin using the abovementioned hemoglobin sensor according to an embodiment of the invention. In step S601, a handheld hemoglobin sensor with a light emitting unit is provided and the light emitting unit is operated to emit a plurality of incident light beams into a solution in a container, wherein the incident light beams are not aimed directly at an excreta in the same container; the container is, for instance, a toilet. The incident light beams are emitted into the solution and produce a plurality of detection light beams. The container is a toilet, a bedpan, a urinal, a portable urinal, or a spittoon.

In one embodiment of the invention, when the incident light beams are emitted into and aimed at the solution, they also penetrate the solution and hit a light reflector and thereby producing the detection light beams, wherein the light reflector is an inner surface of the container (toilet).

Step S603 is to provide a light sensing unit to receive the detection light beams and generate a detection signal. A data processor is then provided to receive the detection signal and generate a detection result data in step S605. In Step S607, a result presentation unit is provided to receive the detection result data and present a detection result of occult blood, such as positive or negative.

Figure 11:
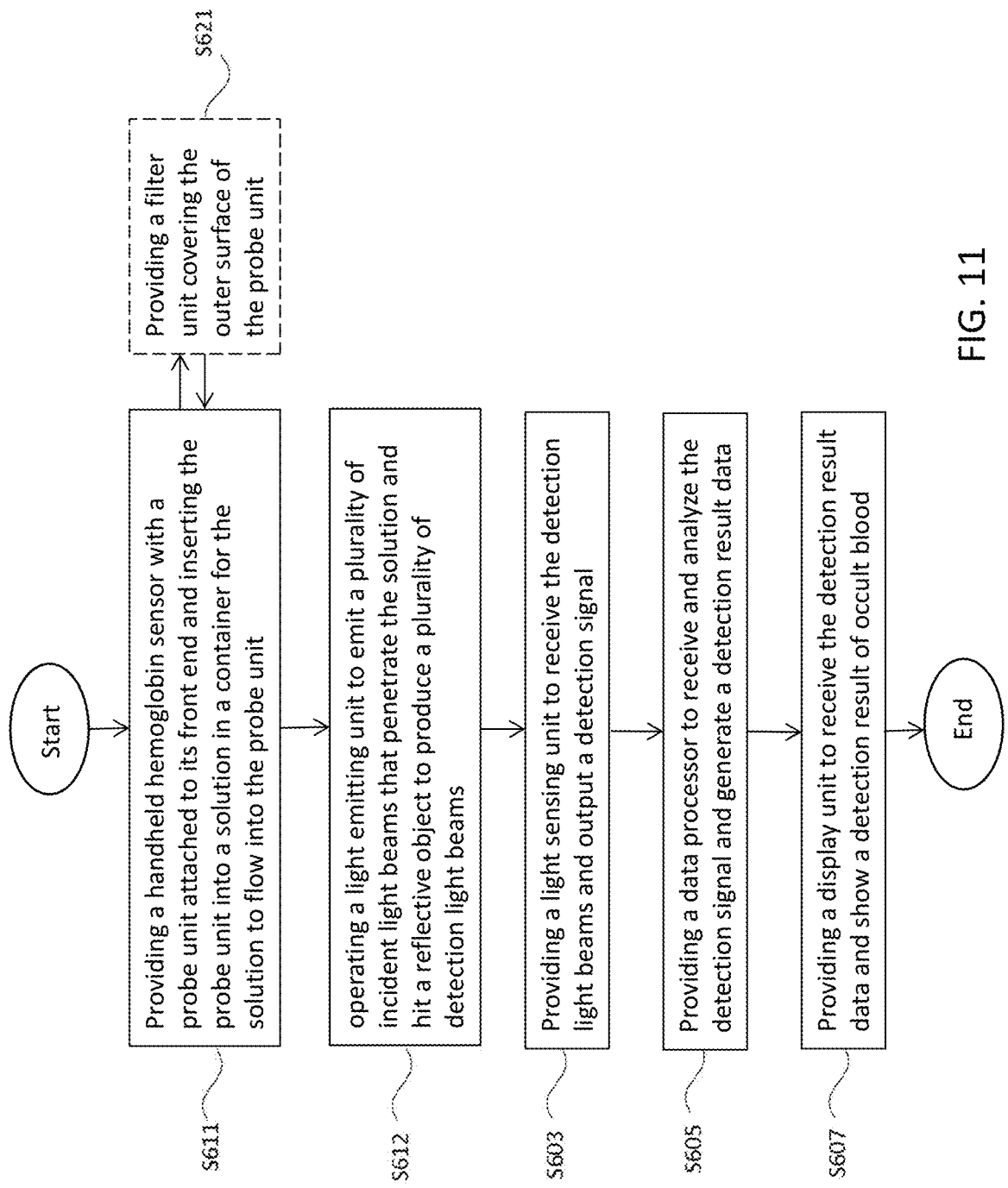
FIG. 11 is a flow chart of a hemoglobin detection method according to another embodiment of the invention.

FIG. 11 is a flow chart of a method for detecting hemoglobin according to another embodiment of the invention, wherein Step S601 in the previous embodiment is replaced by steps S611 and S612. Step S611 is to provide a handheld hemoglobin sensor with a probe unit attached to its front end and to insert the probe unit into a solution in a container, like a toilet, such that the solution flows into the probe unit, wherein the probe unit is a hollow tube and the probe unit is not inserted directly into the excreta like feces.

In step 612, a light emitting unit is operated to emit a plurality of incident light beams into the solution in the probe unit. The incident light beams penetrate the solution and hit a light reflector to produce a plurality of detection light beams. Subsequent steps S603, S605, and S607 are then performed.

In yet another embodiment of the hemoglobin detection method of the invention, step S611 further includes an extra step S621. Step S621 is to provide a filter unit for covering the outer surface of the probe unit after the probe unit has been attached to the front end of the hemoglobin sensor. Then, the probe unit together with the filter unit is inserted into the solution in the container (toilet) to cause the solution to pass through the filter unit and flow into the probe unit. The filter unit is used to filter out larger particles of the excreta or impurity in the container. Steps S612, S603, S605, and S607 are then subsequently performed.

In one embodiment of the invention, the light reflector in step S601 is an inner surface of the container and the emission of light into the solution is performed at a region where the solution depth is relatively shallow. As for step S612, the light reflector is an inner surface of the container, an inner surface of the probe unit, or a reflector sheet attached in the probe unit.

In one embodiment of the invention, the detection signal in step S605 is a spectrum or a light intensity value, wherein the spectrum is an absorption spectrum, a fluorescence spectrum, a scattering spectrum, or a Raman spectrum.

In one embodiment of the invention, the wavelengths of the incident light beams in step S601 are in a range between 350 nm-800 nm. The data processor in step S607 determines and generates the detection result data by analyzing whether a characteristic absorption peak value of the absorption spectrum is approximate to 415 nm, 541 nm, or 577 nm.

In one embodiment of the invention, the light emitting unit in step S601 includes four light emitting diodes, three of which have wavelength peak values of 375 nm, 395 nm, and 415 nm and one of which is a white light emitting diode. In one embodiment of the invention, the light emitting unit further includes four slit units corresponding to the four light emitting diodes.

In the aforementioned embodiments, the incident light beams are mainly aimed at the solution, not the excreta (feces) itself. However, if the test matter is urine or phlegm where the excreta and the solution in the toilet cannot be told apart, then the incident light beams are aimed directly at the matter itself existing in the toilet.

The above disclosure is only the preferred embodiment of the present invention, and not used for limiting the scope of the present invention. All equivalent variations and modifications on the basis of shapes, structures, features and spirits described in claims of the present invention should be included in the claims of the present invention.

The invention claimed is:

1. A hemoglobin sensor comprising:
a handheld housing comprising:
a light emitting unit disposed in the handheld housing for emitting a plurality of incident light beams having wavelengths in a range of 350 nm to 800 nm;
an operating interface connected to the light emitting unit for activating the light emitting unit to emit the incident light beams toward a front end of the handheld housing;
a light sensing unit disposed in the handheld housing for receiving a plurality of detection light beams and generating a detection signal; and
a data processor connected to the light sensing unit for receiving the detection signal and generating a detection result data, wherein the incident light beams are aimed at a solution that is in a container having an excreta and external of the handheld housing, and the incident light beams penetrate the solution and produce the detection light beams; and
a probe unit and a light reflector, wherein the probe unit is a hollow tube having at least one through hole and is attachable to the front end of the handheld housing, the light reflector is disposed at a front end of the probe unit for producing the detection light beams when the incident light beams hit the light reflector after penetrating the solution, and the solution flows into and out of the probe unit via the through hole;
a filter unit covering the probe unit and being passable by the solution;
a display unit for receiving the detection result data and presenting a detection result.

2. The hemoglobin sensor of claim 1, wherein the container is a toilet, a bedpan, a urinal, a portable urinal, or a spittoon.

3. The hemoglobin sensor of claim 1, further comprising a light guide unit disposed in the handheld housing at a front end of the light sensing unit, for collecting and transmitting the detection light beams.

4. The hemoglobin sensor of claim 1, wherein the display unit is disposed on a surface of the handheld housing or in a remote electronic device external of the handheld housing.

5. The hemoglobin sensor of claim 1, wherein the light reflector is an inner surface of the probe unit or a reflector sheet.

6. The hemoglobin sensor of claim 1, wherein the data processor generates the detection result data by analyzing whether a wavelength peak value in the detection signal is approximate to 415 nm, 541 nm, and 577 nm.

7. The hemoglobin sensor of claim 1, wherein the light emitting unit comprises at least three light emitting diodes, and wavelength peak values of the incident light beams are approximate to 375 nm, 395 nm, and 415 nm, respectively.

8. The hemoglobin sensor of claim 1, wherein the light emitting unit comprises at least four light emitting diodes, one of which is a white light emitting diode.

9. The hemoglobin sensor of claim 1, wherein the detection signal is a spectrum or a light intensity value.

10. The hemoglobin sensor of claim 9, wherein the spectrum is an absorption spectrum, a fluorescence spectrum, a scattering spectrum, or a Raman spectrum.

11. A hemoglobin detection method comprising:
providing a handheld hemoglobin sensor with a light emitting unit;
providing a probe unit attached to a front end of the handheld hemoglobin sensor and inserting the probe unit into a solution;
providing a filter unit covering an outer surface of the probe unit and inserting the filter unit into the solution with the probe unit;
operating the light emitting unit to emit a plurality of incident light beams that penetrate the solution in a container having an excreta and produce a plurality of detection light beams, wherein the container is a toilet, a bedpan, a urinal, a portable urinal, or a spittoon;
providing a light sensing unit to receive the detection light beams and generate a detection signal;
providing a data processor to receive the detection signal and generate a detection result data; and
providing a display unit to receive the detection result data and present a detection result.

12. The hemoglobin detection method of claim 11, wherein wavelengths of the incident light beams are in a range of 350 nm to 800 nm, and the data processor generates the detection result data by analyzing whether a wavelength peak value in the detection signal is approximate to 415 nm, 541 nm, and 577 nm.

* * * * *